United States Patent [19]
Vaillancourt

[11] Patent Number: 5,360,408
[45] Date of Patent: Nov. 1, 1994

[54] SHIELDED HYPODERMIC NEEDLE ASSEMBLY AND A SHIELD ASSEMBLY FOR A HYPODERMIC NEEDLE

[76] Inventor: Vincent L. Vaillancourt, 14 Bunyan Dr., Livingston, N.J. 07039

[21] Appl. No.: 976,470
[22] Filed: Nov. 16, 1992
[51] Int. Cl.⁵ .............................................. A61M 5/32
[52] U.S. Cl. ...................................... 604/198; 604/263
[58] Field of Search .............. 604/110, 187, 192, 198, 604/263

[56] References Cited
U.S. PATENT DOCUMENTS

| | | | |
|---|---|---|---|
| 5,059,184 | 10/1991 | Dyke | 604/263 X |
| 5,104,384 | 4/1992 | Parry | 604/192 |
| 5,201,708 | 4/1993 | Martin | 604/110 |
| 5,222,947 | 6/1993 | D'Amico | 604/198 |
| 5,246,428 | 9/1993 | Falknor | 604/198 |

Primary Examiner—John D. Yasko
Attorney, Agent, or Firm—Francis C. Hand

[57] ABSTRACT

The shield assembly for a hypodermic needle includes a sleeve which is mounted on a syringe housing and a tubular shield which can be moved between an extended position over the hypodermic needle to a retracted position partially within the sleeve to expose the hypodermic needle. A resilient strip is used to engage in a recess of the shield to lock the shield in the extended position. A slide block is also provided to disengage the resilient strip from the shield to permit retraction of the shield and consequent exposure of a hypodermic needle. A spring serves to return the shield to the extended position.

26 Claims, 2 Drawing Sheets

SHIELDED HYPODERMIC NEEDLE ASSEMBLY AND A SHIELD ASSEMBLY FOR A HYPODERMIC NEEDLE

This invention relates to a shielded hypodermic needle assembly and to a shield assembly for a hypodermic needle.

As is known, one major problem with a hypodermic needle as well as other needles is the threat of cutting oneself or another thereby exposing a blood vessel to the environment. This has become especially important in a hospital atmosphere where AIDS patients or AIDS members of the staff can infect others by having their blood interact, for example, by touching another person.

Various techniques have been forwarded to overcome this problem. These techniques include placing a shield over the needle after use; allowing for only a one time use of the needle with an automatic covering system which prevents further use, and various types of means for remotely shielding the needle after use. However, in none of these cases does the needle remain totally protected during an entire procedure. Further, if the needle is used twice, there is no provision to handle more than one use of the needle.

In practice, needles are almost always used at least twice. That is, in a first use of a needle which is attached to a syringe (a majority of the needle usage), the needle is used to puncture a drug vial and, if already constituted, draw the drug (or other medication) into the syringe. If the drug has not been reconstituted, for example, being in a powder state, then the needle must be used to reconstitute the drug. Once the syringe has been filled with medication and is otherwise ready for use on a patient, the needle of the syringe is used to pierce a septum on an I.V. Administration Set or to alternately puncture the body of the patient directly. This is followed by the administration of the drug. The needle is then withdrawn and the exposed needle is, in some fashion, shielded and ultimately discarded.

Accordingly, it is an object of the invention to provide a hypodermic needle with a continuous type of protection.

It is another object of the invention to render a hypodermic needle "stickless".

It is another object of the invention to provide a relatively simple structure for maintaining a hypodermic needle in a shielded condition during use.

It is another object of the invention to provide a relatively simple structure to maintain a hypodermic needle in a shielded condition from one use to another use as well as in between uses.

It is another object of the invention to provide a shielded hypodermic needle which permits a practitioner to visually determine if the needle is in a shielded condition.

Briefly, the invention provides a shielded hypodermic needle assembly comprising a housing defining a chamber, a hollow hypodermic needle mounted in and extending from said housing with the needle having a lumen in communication with the chamber, and a shield disposed concentrically about the needle for movement relative to the housing between an extended position completely enclosing the needle therein and a retracted position exposing the distal end of the needle. In addition, the assembly includes a locking means which is mounted on the housing for releasably locking the shield in the extended position.

In one embodiment, the needle assembly includes a biasing means between the housing and the shield for biasing the shield from the retracted position to the extended position. In this embodiment, the biasing means serves to positively move the shield to the extended position when the needle is not in a condition of use. The biasing means should, however, not have a biasing strength which would impair the use of the needle, for example, for piercing through a drug vial, for piercing a septum on an I.V. Administration Set or for penetrating into a blood vessel of a patient.

The needle assembly can be used in a generally conventional fashion. In this respect, the locking means for the shield is first actuated so as to permit the shield to be moved from an extended position over the needle to a retracted position exposing the needle. When the assembly is in this condition, the needle can be inserted into a drug vial to receive medication or passed into a blood vessel of a patient in order to dispense medication. After the needle has been used and has been retracted from the drug vial or blood vessel, the shield can be moved into the extended position and locked in place by the locking means so as to completely encircle the needle. In this way, the needle can be rendered stickless. In this respect, the shield can be made of any suitable material which can be readily manipulated by a user and which can provide security against inadvertent sticking of a person with the sharp end of the needle.

In the embodiment using the biasing means, the shield is automatically returned to the extended position upon removal of the needle from a drug vial or blood vessel. In this respect, the biasing means may take any suitable form. For example, the biasing means may be in the form of a coil spring, a collapsible resilient tube and the like.

In still another embodiment, in order to add some redundancy of safety, a manually operated unlocking means is provided for releasing the locking means in order to allow movement of the shield from the extended position to the retracted position. In this embodiment, there is a need to actuate the unlocking means in a positive manner by the user so that the locking means can be released. Thus, visual inspection of the needle assembly will indicate that the assembly is in a locked condition if the unlocking means is in a retracted position relative to a triggering or arming position. Any suitable type of unlocking means may be used. In this respect, the unlocking means acts as a safety catch.

In one embodiment, the shield may include a recess in an outer surface while the locking means includes a sleeve mounted on and extending from the housing concentrically about the shield. In this case, the sleeve has an elongated resilient strip which extends coaxially of the sleeve with the strip having an inwardly directed tang at a free distal end for engaging in the recess of the shield in order to lock the shield in the extended position. Such a locking means is of relatively rigid construction and requires a positive force in order to release the tang from the recess. With this embodiment, the unlocking means may be in the form of a slide block which is slidably mounted in an elongated slot in the sleeve for sliding along the slot between the resilient strip and the sleeve. In this respect, the slide block is sized and positioned to deflect the strip in a direction away from the sleeve in order to remove the tang from the recess in the sleeve and, thus, bring about an unlocking of the shield for movement from the extended position to the retracted position. Visual inspection of this embodiment will permit a determination as to whether the slide block is in a position which permits engagement of the tang in the recess of the sleeve or in a release position in which the resilient strip and tang are lifted away from the recess in the sleeve.

In still another embodiment, the shield may be provided with an opening at an intermediate point to permit viewing of the needle. In this way, the user can first determine if there is a needle within the shield prior to use.

Typically, the shield is slidably mounted in sealed relation on the needle at a proximal end of the shield. In addition, in one embodiment, a membrane is provided at a distal end of the shield to form a sealed chamber within the shield to contain the needle. This membrane may be pierced by the needle when the needle is to be used. Upon extension of the shield passed the needle, the membrane closes on itself to reseal the chamber containing the needle.

In still another embodiment, the shield may be provided with a detent on the outer surface or some other type of structure for releasably engaging with the tang of the locking means when the shield is in the retracted position. This permits the locking means to lock the shield not only in the extended position relative to the needle but also serves to lock the shield in the retracted position relative to the needle. As above, this embodiment may be provided with an unlocking means which must be manually operated in order to release the locking means from the detent.

The hypodermic needle assembly is otherwise of conventional construction, for example, employing a syringe which defines the housing in which the hollow hypodermic needle is mounted. In this respect, the sleeve of the locking means is secured on the housing of the syringe in a permanent manner or a releasable manner.

The invention also provides a shield assembly which can be retrofitted onto existing syringes or separately made from a syringe. This shield assembly is composed of a sleeve which can be mounted on a syringe housing, a shield which is slidably mounted in the sleeve, a resilient strip integral with the sleeve to effect locking of the shield in an extended position relative to the sleeve and an unlocking means for releasing the resilient strip as described above. In addition, this shield assembly may include a biasing means, such as a coil spring, which is located within the sleeve to be fitted over a needle of a syringe when the sleeve is affixed to the syringe.

These and other objects and advantages of the invention will become more apparent from the following detailed description taken in conjunction with the accompanying drawings wherein.

Figure 1:
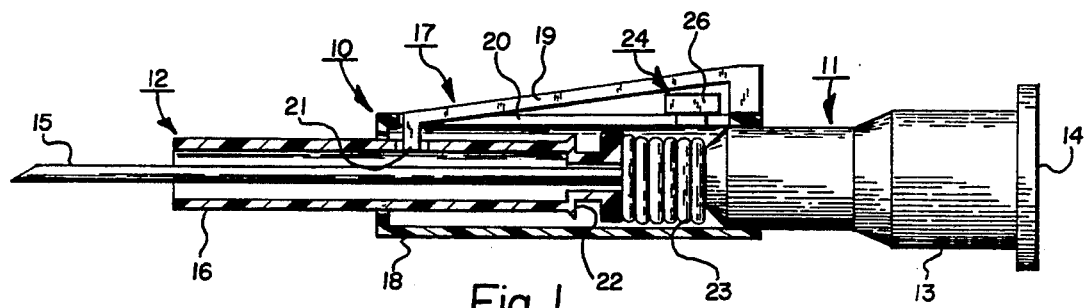
FIG. 1 illustrates a part cross-sectional view of a shield assembly mounted on a syringe in accordance with the invention.

Referring to FIG. 1, the shielded hypodermic needle assembly 10 comprises a syringe 11 and a shield assembly 12 mounted on the syringe 11.

The syringe 11 is of conventional construction and includes a housing 13 which defines a chamber 14 for receiving fluid, such as medications and the like. In addition, the syringe 11 has a hollow hypodermic needle 15 extending from the housing 13 and which has a lumen in communication with the chamber 14 in order to convey fluids therefrom and therethrough.

The shield assembly 12 is mounted on the housing 13 of the syringe 11, for example, in a permanent manner by means of a suitable adhesive. Alternatively, the shield assembly 12 may be mounted on the housing 13 in a removable manner, for example by being threaded onto the housing 13.

The shield assembly 12 includes a shield 16 which is disposed concentrically about the needle 15 for movement relative to the syringe housing 13 between an extended position (see FIG. 3) completely enclosing the needle 15 and a retracted position (see FIG. 1) exposing a distal end of the needle 15. The shield 16 may be of tubular construction such as one having a circular cross section or polygonal cross section.

The shield assembly 12 also includes a locking means 17 mounted on the syringe housing 13 for releasably locking the shield 16 in the extended position. This locking means 17 includes a sleeve 18 which is mounted on and which extends from the syringe housing 13 concentrically about the shield 16 and an elongated resilient strip 19 which is integral with and which extends coaxially of the sleeve 18. As indicated, the sleeve 18 is provided with a slot 20 to permit a distal end of the strip 19 to pass therethrough. In addition, the free distal end of the strip 19 has a radially inwardly directed tang 21.

Figure 3:
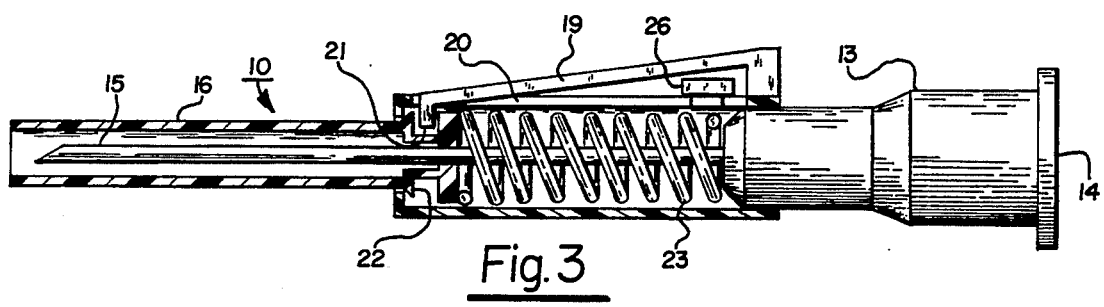
FIG. 3 illustrates a view of the shield assembly of FIG. 1 in a locked extended position.

The shield 16 includes an annular recess 22 in the outer surface at a proximal end for receiving the tang 21 when the shield 16 is in the extended position (see FIG. 3). Alternatively, the recess 22 may be replaced by any other suitable means such as an annular collar or raised detent which serves as an abutment for engaging against the tang 21 when the shield 16 is in the extended position.

As shown in FIG. 1, a biasing means 23, for example, in the form of a coil spring, is disposed between the syringe housing 13 and the shield 16 for biasing the shield 16 from the retracted position shown in FIG. 1 to the extended position shown in FIG. 3.

Figure 4:
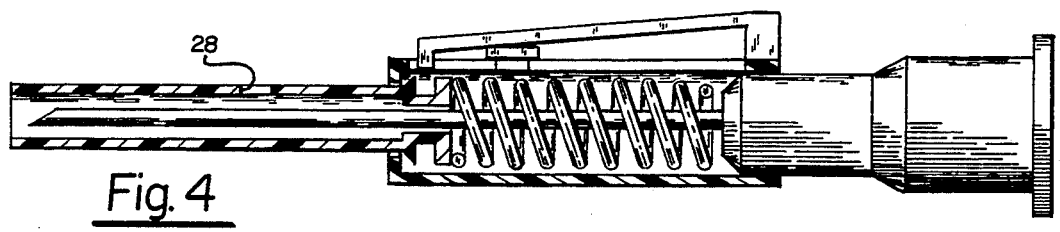
FIG. 4 illustrates a view similar to FIG. 3 at a point in time when the locking means of the shield assembly has been released.

Also, as shown in FIG. 1, the shield assembly 12 includes an manually operated unlocking means 24 for releasing the resilient strip 19 of the locking means 17 in order to allow movement of the shield 16 from the extended position to the retracted position, for example, when the needle 15 is to be exposed for use. This unlocking means 24 is in the form of a slide block which is slidably mounted on the sleeve 18 to slide within the slot 20. As shown in FIG. 1, the slide block 24 has a depending stem 25 which is sized to slide in the slot 20 and an enlarged head 26 which is sized to rest on the sleeve 18. The head 26 of the slide block 24 is positioned between the sleeve 18 and the resilient strip 19 in order to deflect the strip 19 in a direction away from the sleeve 18 as the block 24 moves from right to left, as viewed, so as to remove the tang 21 from the recess 22 in the shield 16 as shown in FIG. 4. This serves to unlock the shield 16.

In use, the syringe 11 and shield assembly 12 form a shielded hypodermic needle assembly 10 which can be transported from place to place with the shield 16 in the locked extended position over the hypodermic needle 15. When the needle assembly 10 is to be used, the slide block 24 is manually operated so as to be slid forwardly thereby lifting the free end of the resilient strip 19, for example into the position as shown in FIG. 4. At this time, the shield 16 is free to move against the biasing force of the spring 23. For example, if the hypodermic needle 15 is to be inserted into a vial (not shown) in order to introduce medication into the chamber 14 of the syringe housing 13, the shield 16 moves to the retracted position against the force of the spring 23 as the hollow hypodermic needle 15 pierces through a septum of the vial. In similar fashion, when the needle 15 is inserted into a blood vessel of a patient, the shield 16 would move towards the retracted position against the force of the spring 23.

Once the needle 15 is removed from the septum of a vial or an Administration Set or from a blood vessel of a patient, the spring 23 urges the shield 16 towards the extended position. With the slide block 24 returned to a retracted position, the resilient strip 19 is free to move into the slot 20 of the sleeve 18 so that the tang 21 on the distal end of the strip 19 is able to snap into the recess 22 of the shield 16.

The shield assembly 12 can be made of any suitable material. For example, the shield 16 may be made of a translucent material so that the needle 15 can be viewed therein.

Figure 2:
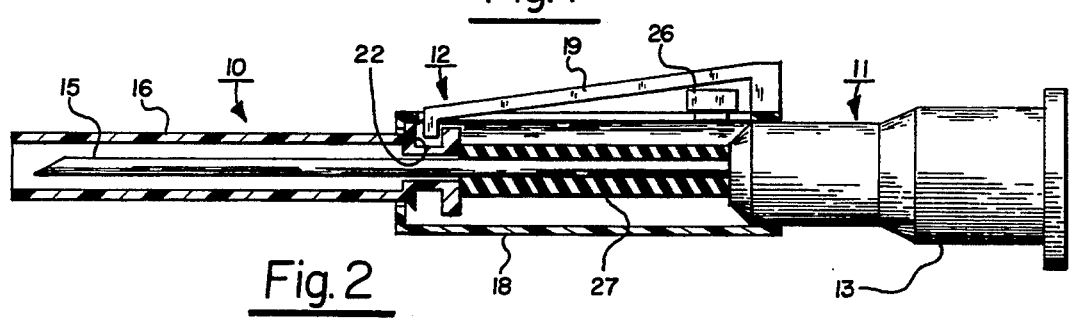
FIG. 2 illustrates a part cross-sectional view of a shield assembly employing a modified biasing means in accordance with the invention.

Referring to FIG. 2, wherein like reference characters indicate like parts as above, the biasing means may be in the form of a resilient tube 26 for biasing the shield 16 from a retracted position into the extended position as shown.

Figure 5:
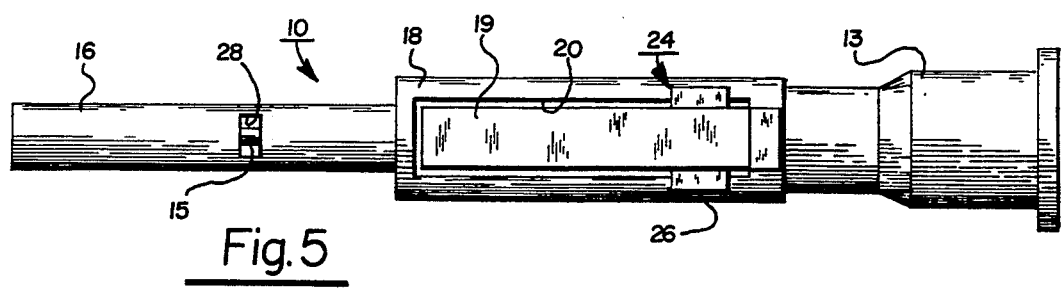
FIG. 5 illustrates a plan view of the shielded hypodermic needle of FIG. 3 in the locked position.

Referring to FIGS. 4 and 5, wherein like reference characters indicate like parts as above, the shield 16 may be provided with an opening 28 in the outer surface at an intermediate position for viewing of the needle 15.

Figure 6:
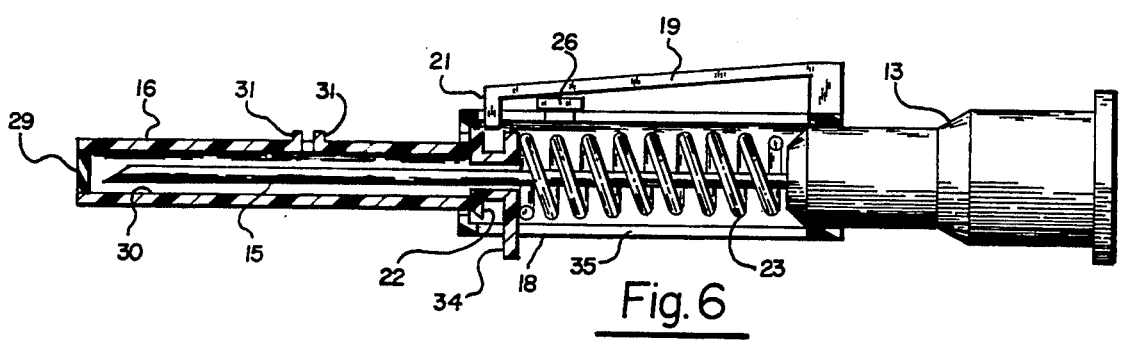
FIG. 6 illustrates a view similar to FIG. 3 of a modified shield having a membrane at a distal end and an intermediate locking tang.

Referring to FIG. 6, the shield 16 may be provided with a membrane 29 at the distal end while the proximal end of the shield is slidably mounted on the needle 15. In this way, a sealed chamber 30 may be formed within the shield 16 to enclose the needle 15. In this embodiment, when the shield 16 is extended into the extended position, the membrane 29 is made of a material which will self-seal.

In addition, as shown in FIG. 6, the shield 16 may be provided with a detent 31 on the outer surface for releaseably engaging with the tang 21 of the resilient strip 19, that is, the locking means 17 when the shield 16 is in the retracted position. In this way, the strip 19 may serve to lock the shield 16 not only in the extended position as shown in FIG. 3, but also in a retracted position corresponding to that as shown in FIG. 1.

Figure 7:
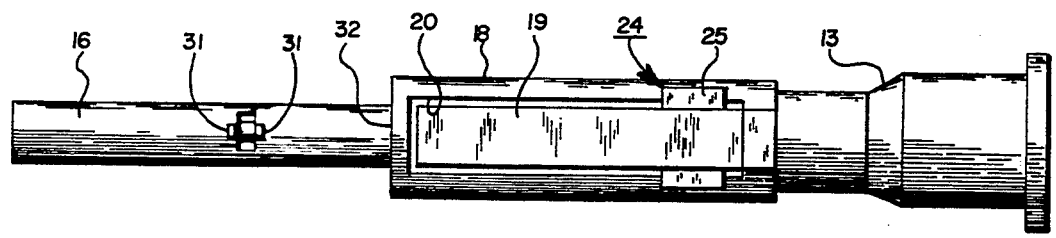
FIG. 7 illustrates a plan view of the needle assembly of FIG. 6.

As indicated in FIG. 7, the sleeve 18 is provided with a slot 32 to permit passage of the detent 31 when the shield 16 is moved into the retracted position.

As further illustrated, the shield 16 may have a detent 33 extending radially outwardly to pass through the slot 34 in the sleeve 18. This detent 33 permits the shield 16 to be manually retracted by grasping and pulling of the detent 33 rearwardly, as viewed, that is to the right as shown in FIG. 6. The detent 33 allows the shield to be retracted without a need to have the shield 16 actually abut against another object.

As indicated, the slot 34 extends from near the distal end of the sleeve 18 to an intermediate of the sleeve 18. The length of the slot 34 is such as to permit the shield 16 to be retracted to a fully retracted position relative to the hollow needle 15.

The invention thus provides a shielded hypodermic needle assembly which can be transported from place to place while a shield is securely held in a locked position over the hypodermic needle of the assembly. Further, the shield may be unlocked from time to time to permit exposure of the needle for use without need to remove the shield from the remainder of the assembly.

Further, the invention provides a shield assembly which can be separately manufactured from the syringe and subsequently retrofitted or otherwise mounted on the syringe in overlying relation to the hypodermic needle extending from a housing of the syringe.

Still further, the invention provides a shield assembly for a hypodermic needle which permits the needle to have multiple uses while maintaining the needle in a covered manner between uses. For example, the needle may be inserted into a medication vial in order to draw medication into the syringe and subsequently may be used to pierce through a blood vessel of a patient or through a septum of an Administration Set.

What is claimed is:

1. A shielded hypodermic needle assembly comprising
   a housing defining a chamber;
   a hollow hypodermic needle mounted in and extending from said housing, said needle having a lumen in communication with said chamber;
   a shield disposed concentrically about said needle for movement relative to said housing between an extended position completely enclosing said needle therein and a retracted position exposing a distal end of said needle;
   locking means mounted on said housing for releasably locking said shield in said extended position; and
   manually operated unlocking means for releasing said locking means to allow movement of said shield from said extended position to said retracted position.

2. A shielded hypodermic needle assembly as set forth in claim 1 which further comprises biasing means between said housing and said shield for biasing said shield from said retracted position to said extended position.

3. A shielded hypodermic needle assembly as set forth in claim 26 which further comprises a manually operated unlocking means between said strip and said sleeve for deflecting said strip in a direction away from said sleeve to remove said tang from said recess in said sleeve to unlock said shield for movement from said extended position to said retracted position.

4. A shielded hypodermic needle assembly as set forth in claim 3 wherein said sleeve has an elongated slot receiving said strip therein and said unlocking means is a slide block slidably mounted on said sleeve for sliding along said slot.

5. A shielded hypodermic needle assembly as set forth in claim 4 which further comprises biasing means between said housing and said shield for biasing said shield from said retracted position to extended position.

6. A shielded hypodermic needle assembly as set forth in claim 3 wherein said shield has an opening in said outer surface thereof for viewing of said needle.

7. A shielded hypodermic needle as set forth in claim 6 wherein said opening in said shield is positioned to receive said tang of said strip with said shield in said retracted position for locking of said shield in said retracted position.

8. A shielded hypodermic needle assembly as set forth in claim 1 wherein said shield is slidably mounted in sealed relation on said needle at a proximal end of said shield and which further comprises a membrane at a distal end of said shield to form a sealed chamber within said shield containing said needle.

9. A shielded hypodermic needle assembly as set forth in claim 8 wherein said shield has a detent on an outer surface for releasably engaging with said locking means in said retracted position of said shield.

10. A shielded hypodermic needle assembly as set forth in claim 9 wherein said shield includes a recess in an outer surface and said locking means includes a sleeve mounted on and extending from said housing concentrically about said shield, said sleeve having an elongated resilient strip extending coaxially of said sleeve, said strip having an inwardly directed tang at a distal end for engaging in said recess of said shield to lock said shield in said extended position.

11. A shielded hypodermic needle assembly as set forth in claim 10 which further comprises a manually operated unlocking means between said strip and said sleeve for deflecting said strip in a direction away from said sleeve to remove said tang from said recess in said sleeve to unlock said shield for movement from said extended position to said retracted position.

12. A shield and hypodermic needle as set forth in claim 1 which further comprises a detent extending radially outwardly from said shield for manual grasping thereof to move said shield from said extended position to said retracted position.

13. A shield and hypodermic need as set forth in claim 12 wherein said locking means includes a sleeve mounted on and extending from said housing concentrically about said shield, said sleeve having an elongated slot slidably receiving said detent therein.

14. In combination,
a syringe having a housing defining a chamber and a hollow hypodermic needle extending from said housing and communicating with said chamber;
a shield disposed about said needle and movably mounted relative to said needle for movement between an extended position enclosing said needle therein and a retracted position exposing a distal end of said needle;
locking means mounted on said housing for releasably locking said shield in said extended position; and
manually operated unlocking means for releasing said locking means to allow movement of said shield from said extended position to said retracted position.

15. The combination as set forth in claim 14 which further comprises biasing means between said housing and said shield for biasing said shield from said retracted position to extended position.

16. The combination as set forth in claim 14 wherein said shield includes a recess and said locking means includes a sleeve mounted on said housing and slidably receiving said shield therein and a resilient strip on said sleeve having a tang at a distal end for engaging in said recess of said shield to lock said shield in said extended position.

17. The combination as set forth in claim 16 wherein said manually operated unlocking means is disposed between said strip and said sleeve for deflecting said strip in a direction away from said sleeve to remove said tang from said recess in said sleeve to unlock said shield for movement from said extended position to said retracted position.

18. The combination as set forth in claim 17 wherein said sleeve has an elongated slot receiving said strip therein and said unlocking means is a slide block slidably mounted on said sleeve for sliding along said slot.

19. The combination as set forth in claim 14 wherein said needle is slidably mounted in sealed relation to said shield at a proximal end thereof and which further comprises a membrane at a distal end of said shield to form a sealed chamber within said shield containing said needle.

20. A shield assembly for a hypodermic needle comprising
a sleeve for mounting on a syringe housing;
a tubular shield mounted in said sleeve for movement between an extended position relative to said sleeve to enclose a hypodermic needle therein and a retracted position relative to said sleeve to expose a hypodermic needle, said shield having a recess in an outer surface;
an elongated strip extending coaxially of said sleeve and having a free end for selectively engaging in said recess to lock said shield in said extended position; and
a manually operated unlocking means between said strip and said sleeve for deflecting said strip away from said recess to unlock said shield for movement from said extended position to said retracted position.

21. A shield assembly as set forth in claim 20 wherein said shield is made of translucent material for viewing of a hypodermic needle therein.

22. A shield assembly as set forth in claim 20 wherein said shield has an opening in said outer surface thereof for viewing of a hypodermic needle therein.

23. A shield assembly as set forth in claim 20 wherein said sleeve has a slot and said unlocking means is a slide block slidably mounted on said sleeve under said strip for sliding along said slot.

24. A shield assembly as set forth in claim 20 wherein said strip is resilient and is integral with said sleeve.

25. A shield assembly as set forth in claim 20 which further comprises biasing means in said sleeve for biasing said shield from said retracted position to said extended position.

26. A shielded hypodermic needle assembly comprising
a housing defining a chamber;
a hollow hypodermic needle mounted in and extending from said housing, said needle having a lumen in communication with said chamber;
a shield disposed concentrically about said needle for movement relative to said housing between an extended position completely enclosing said needle therein and a retracted position exposing a distal end of said needle, said shield having a recess in an outer surface; and
locking means mounted on said housing for releasably locking said shield in said extended position, said locking means including a sleeve mounted on and extending from said housing concentrically about said shield, said sleeve having an elongated resilient strip extending coaxially of said sleeve, said strip having an inwardly directed tang at a distal end for engaging in said recess of said shield to lock said shield in said extended position.

* * * * *